(12) United States Patent
Hopkins et al.

(10) Patent No.: US 11,756,044 B1
(45) Date of Patent: Sep. 12, 2023

(54) METHOD, APPARATUS AND COMPUTER PROGRAM PRODUCT FOR CONDUCTING A MULTI-STAGE VERIFICATION

(71) Applicant: McKesson Corporation, Irving, TX (US)

(72) Inventors: Stacy Hopkins, Tucker, GA (US); Vickie Andros, Atlanta, GA (US)

(73) Assignee: MCKESSON CORPORATION, Irving, TX (US)

( * ) Notice: Subject to any disclaimer, the term of this patent is extended or adjusted under 35 U.S.C. 154(b) by 0 days.

(21) Appl. No.: 16/918,159

(22) Filed: Jul. 1, 2020

(51) Int. Cl.
*G06Q 20/00* (2012.01)
*G06Q 20/42* (2012.01)

(52) U.S. Cl.
CPC .................... *G06Q 20/42* (2013.01)

(58) Field of Classification Search
CPC ....... G06Q 10/105; G06Q 20/42; G16H 20/10
See application file for complete search history.

(56) References Cited

U.S. PATENT DOCUMENTS

| | | | | |
|---|---|---|---|---|
| 7,457,950 B1* | 11/2008 | Brickell | .................. | G06F 21/33 705/317 |
| 8,036,913 B1* | 10/2011 | Pinsonneault | ......... | G06Q 10/10 705/2 |
| 10,366,784 B1* | 7/2019 | Eller | ...................... | G16H 10/60 |
| 2012/0016687 A1 | 1/2012 | Dhavle et al. | | |
| 2012/0150563 A1* | 6/2012 | Carroll | .................. | G06Q 10/06 705/2 |

(Continued)

FOREIGN PATENT DOCUMENTS

| | | |
|---|---|---|
| CA | 2495018 C | 6/2013 |
| CA | 2552056 C | 6/2015 |

(Continued)

OTHER PUBLICATIONS

A Framework for Checking Integrity Constraints in a Distributed Database Published in: 2008 Third International Conference on Convergence and Hybrid Information Technology (vol. 1, pp. 644-650) Authors: A.A. Alwan • H. Ibrahim • N.I. Udzir (Year: 2008).*

(Continued)

*Primary Examiner* — Bruce I Ebersman
*Assistant Examiner* — John A Anderson
(74) *Attorney, Agent, or Firm* — ALSTON & BIRD LLP

(57) ABSTRACT

A method, apparatus and computer program product efficiently verify a transaction, such as an order, in accordance with a multi-stage verification process. In a method, data is extracted from an order submitted pursuant to a program having a plurality of verification qualifications. The method performs a first set of verification checks and, in an instance in which the first set of verification checks is satisfied, the method modifies the order to include a first indication of satisfaction of the first set of verification checks. The method also extracts data from a claim that is based upon the order. The claim includes the first indication that the first set of verification checks was satisfied. The method also performs a second set of verification checks based upon the data extracted from the claim and, in an instance in which the second set of verification checks is satisfied, the method submits the claim via an adjudication network for adjudication.

15 Claims, 9 Drawing Sheets

(56) References Cited

U.S. PATENT DOCUMENTS

| | | | |
|---|---|---|---|
| 2013/0179177 A1 | 7/2013 | Dhavle et al. | |
| 2013/0311205 A1* | 11/2013 | Creswell | G16H 40/60 |
| | | | 705/3 |
| 2016/0055314 A1 | 2/2016 | Anderson et al. | |
| 2016/0188820 A1 | 6/2016 | Brown et al. | |
| 2017/0329921 A1 | 11/2017 | Willard et al. | |
| 2018/0293351 A1 | 10/2018 | Simons et al. | |
| 2020/0005919 A1* | 1/2020 | Hill, Sr. | G16H 10/60 |

FOREIGN PATENT DOCUMENTS

| | | |
|---|---|---|
| CA | 2900718 A1 | 2/2016 |
| CA | 2552057 C | 8/2016 |
| WO | WO 2012/009513 A1 | 1/2012 |

OTHER PUBLICATIONS

Incremental formal verification of hardware Published in: 2011 Formal Methods in Computer-Aided Design (FMCAD) (pp. 135-143) Authors: Chockier, H. • Ivrii, A. • Matsliah, A. • Moran, S. • Nevo, Z (Year: 2011).*

* cited by examiner

METHOD, APPARATUS AND COMPUTER PROGRAM PRODUCT FOR CONDUCTING A MULTI-STAGE VERIFICATION

TECHNOLOGICAL FIELD

An example embodiment relates generally to performance of a multi-stage verification and, more particularly, to performance of a multi-stage verification of an order and, in turn, a claim that is based upon the order.

BACKGROUND

Transactions must oftentimes be verified prior to completing the transaction. For example, a transaction in the form of an order must frequently be verified to ensure that the order is authorized and satisfies any prerequisite conditions prior to filling the order. In this regard, some transactions are submitted pursuant to a program having a plurality of verification qualifications. Such a program may offer advantages to the party placing the order, such as in terms of availability of a product, cost of a product, etc. However, these programs may be subject to certain limitations, such as may be defined by the plurality of verification qualifications. For example, the verification qualifications may impose limitations on the types of products or quantities of products available pursuant to the program, limitations on the parties that may participate in the program, etc. As such, a transaction submitted pursuant to such a program must generally be verified to ensure that the transaction satisfies the qualifications associated with the program prior to processing or completing the transaction. Such a transaction may also be pre-processed to determine that the transaction includes the necessary data elements and may be edited in advance of further processing if any necessary data elements are found to be missing. Thus, upon satisfaction of the verification qualifications for the program, the transaction, such as an order, may be completed, e.g., filled.

The verification of a transaction is generally conducted towards the end of transaction processing and shortly before fulfilling the transaction. While deferring verification until towards the end of the process allows for the transaction to be as complete as possible prior to verification, the deferral of verification until towards the end of the overall process may create inefficiencies if the transaction is not successfully verified. In such an instance, the transaction may have undergone substantial processing prior to the evaluation of the verification qualifications with this processing being rendered unnecessary and having to be repeated upon resubmittal of the transaction in an instance in which the original transaction is not verified as a result of failing to satisfy one or more of the verification qualifications.

For example, some transactions are processed by multiple parties prior to filling the transaction. In an instance in which the verification of the transaction is deferred until the majority, if not all, of the processing of the transaction has been completed, one or more of the parties may have unnecessarily expended resources to process the transaction, which was subsequently terminated as a result of a failure to satisfy the verification qualifications. By way of example, a transaction may originate with one party, but may be subsequently received by and processed by one or more additional parties. In an instance in which the transaction is not eventually verified, the processing of the transaction by the one or more additional parties that did not originate the transaction may have been performed unnecessarily, thereby decreasing the efficiency with which the transaction is processed.

BRIEF SUMMARY

A method, apparatus and computer program product are provided in accordance with an example embodiment in order to more efficiently verify a transaction, thereby conserving resources, such as computing and/or network resources, otherwise consumed in conjunction with the processing of a transaction which subsequently fails to satisfy the verification qualifications. Indeed, the method, apparatus and computer program product of an example embodiment may conduct a multi-stage verification process in order to avoid downstream processing of a transaction, such as by a different party than the party that received and initially processed the transaction, in an instance in which an earlier stage of the verification process indicates that the transaction will fail to satisfy the verification qualifications. In this example embodiment, one or more of the parties otherwise potentially involved in the processing of the transaction may not be required to expend computing resources with respect to the processing of the transaction in an instance in which an earlier stage in the verification process indicates that the transaction will fail to satisfy the verification qualifications.

In an example embodiment, a multi-stage verification method is provided that includes extracting data from an order submitted pursuant to a program having a plurality of verification qualifications. The method performs a first set of verification checks based upon the data extracted from the order. In an instance in which the first set of verification checks is satisfied, the method modifies the order to include a first indication of satisfaction of the first set of verification checks. The method of this example embodiment also includes extracting data from a claim that is based upon the order. In this regard, the claim includes the first indication that the first set of verification checks was satisfied. The method of this example embodiment also includes performing a second set of verification checks based upon the data extracted from the claim. Although some of the verification checks of the first and second sets may be same, the second set of verification checks includes one or more verification checks that are different than the first set of verification checks. In an instance in which the second set of verification checks is satisfied, the method includes submitting the claim via an adjudication network for adjudication.

The method of an example embodiment also includes receiving an approval response following the adjudication. The method of this example embodiment also includes associating a second indication of satisfaction of the second set of verification checks with the approval response.

In another example embodiment, an apparatus is provided that is configured to conduct a multi-stage verification. The apparatus includes a communication interface configured to receive an order submitted pursuant to a program having a plurality of verification qualifications. The apparatus also includes processing circuitry configured to extract data from the order, to perform a first set of verification checks based upon the data extracted from the order and, in an instance in which the first set of verification checks is satisfied, to modify the order to include a first indication of satisfaction of the first set of verification checks. The processing circuitry is also configured to extract data from a claim that is based upon the order and that includes a first indication that the first set of verification checks was satisfied and to perform a second set of verification checks based upon the data extracted from the claim. Although some of the verification checks of the first and second sets may be same, the second set of verification checks includes one or more verification checks that are different than the first set of verification checks. The communication interface of this example embodiment is further configured, in an instance in which the second set of verification checks is satisfied, to submit the claim via an adjudication network for adjudication.

The communication interface of an example embodiment is further configured to receive an approval response following the adjudication. In this example embodiment, the processing circuitry is further configured to associate a second indication of satisfaction of the second set of verification checks with the approval response.

In a further example embodiment, a computer program product is provided that is configured to conduct a multi-stage verification. The computer program product includes at least one non-transitory computer-readable storage medium having computer-executable program code constructions stored therein with the computer-executable program code instructions including program code instructions configured to extract data from an order submitted pursuant to a program having a plurality of verification qualifications. The computer-executable program code instructions also include program code instructions configured to perform a first set of verification checks based upon the data extracted from the order and, in an instance in which the first set of verification checks is satisfied, to modify the order to include a first indication of satisfaction in the first set of verification checks. The computer-executable program coded instructions further include program code instructions configured to extract data from a claim that is based upon the order. The claim includes a first indication that the first set of verification checks was satisfied. The computer-executable program code instructions additionally include program code instructions configured to perform a second set of verification checks based upon the data extracted from the claim. Although some of the verification checks of the first and second sets may be same, the second set of verification checks includes one or more verification checks that are different than the first set of verification checks. The computer-executable program code instructions also include program code instructions configured to submit the claim, in an instance in which the second set of verification checks is satisfied, via an adjudication network for adjudication.

The computer-executable program code instructions of an example embodiment also include program code instructions configured to receive an approval response following the adjudication. In this example embodiment, the computer-executable program code instructions further include program code instructions configured to associate a second indication of satisfaction of the second set of verification checks with the approval response.

In relation to the method, apparatus and computer program product of an example embodiment, the one or more verification checks of the second set of verification checks that are different than the first set of verification checks includes one or more verification checks of information included in or associated with the claim that was not included in or associated with the order. In this regard, the one or more verification checks of the second set of verification checks that are different than the first set of verification checks may include one or more verification checks of action taken in response to the order. Additionally or alternatively, the one or more verification checks of the second set of verification checks may include one or more verification checks that are dependent upon a timing associated with the order. In an example embodiment, the one or more verification checks of the second set of verification checks includes a verification of validity of the first set of verification checks. In another example embodiment, the one or more verification checks of the second set of verification checks include one or more verification checks that were also included in the first set of verification checks.

BRIEF DESCRIPTION OF THE DRAWINGS

Figure 1:
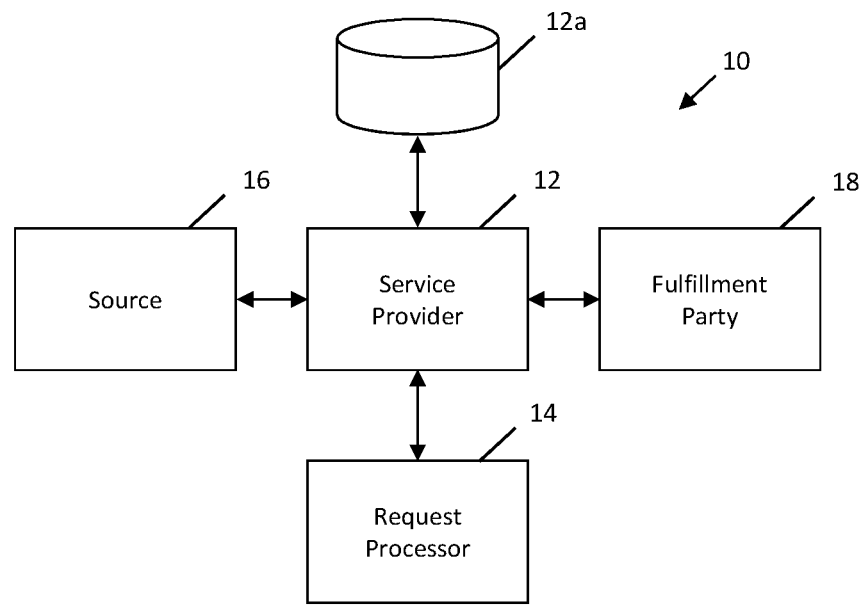
Figure 2:
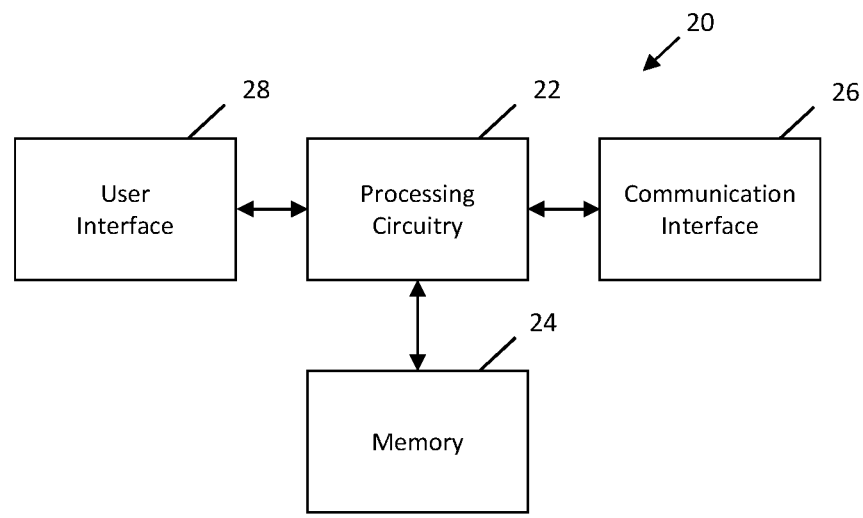
Figure 3A:
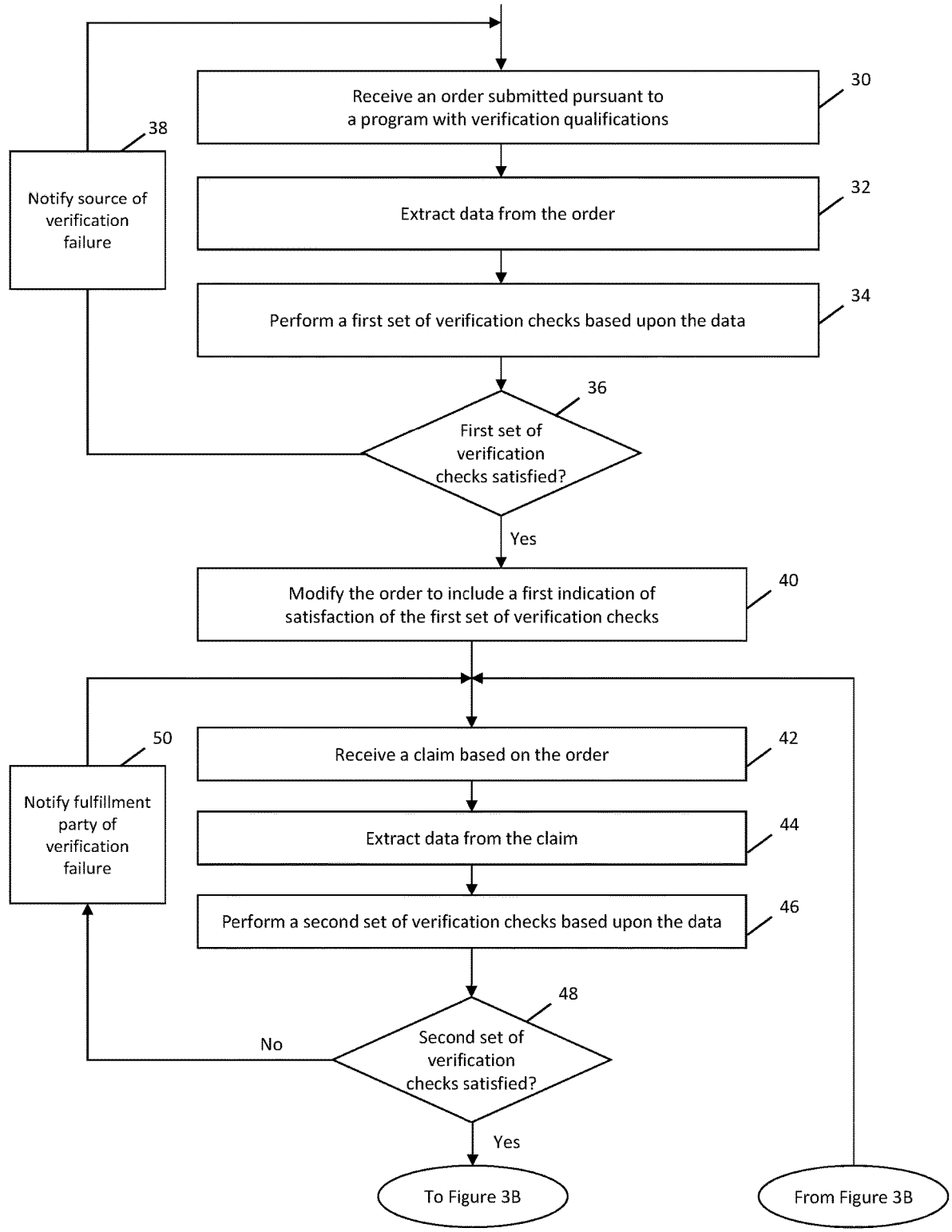
Figure 3B:
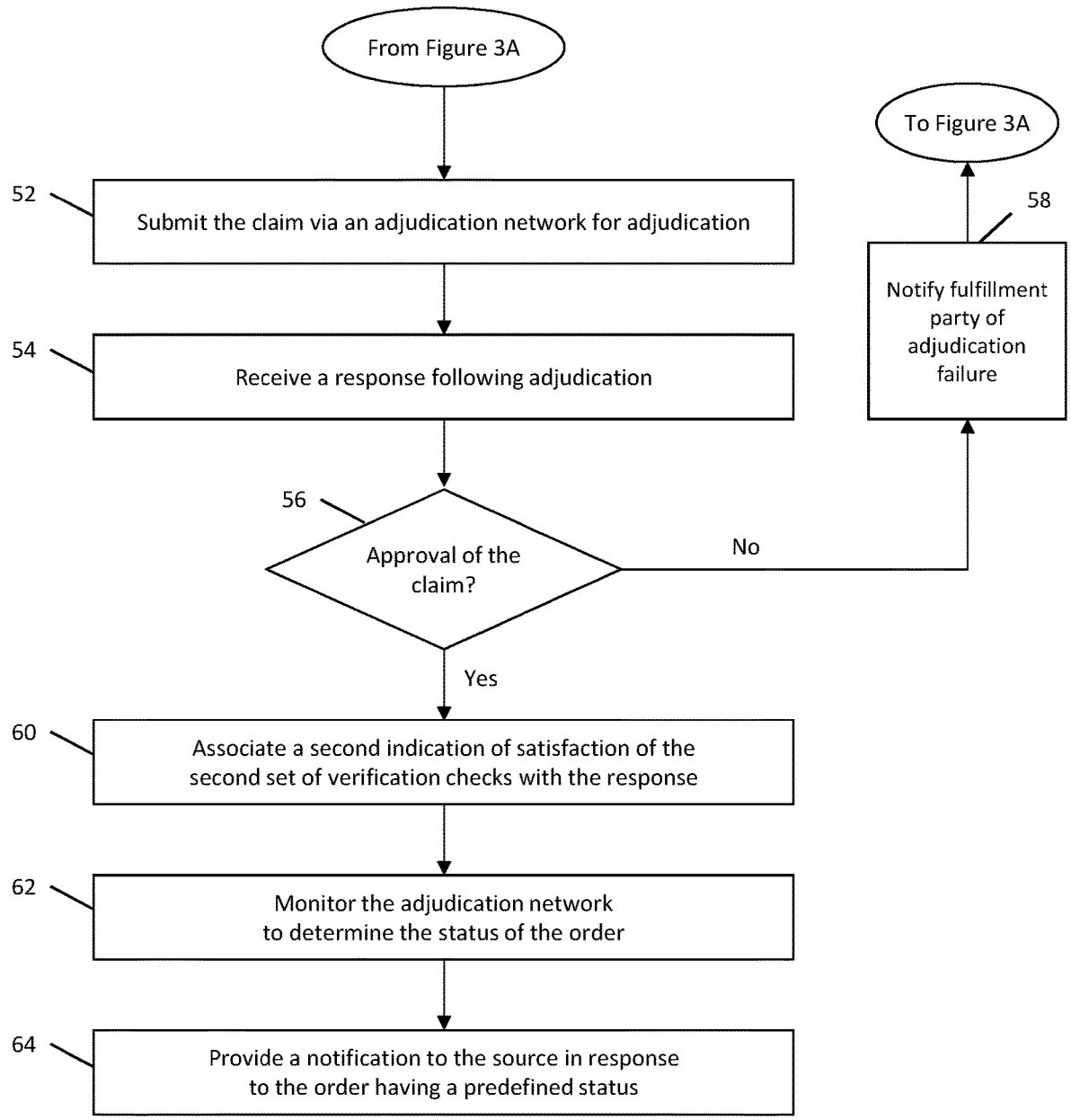
Figure 4:
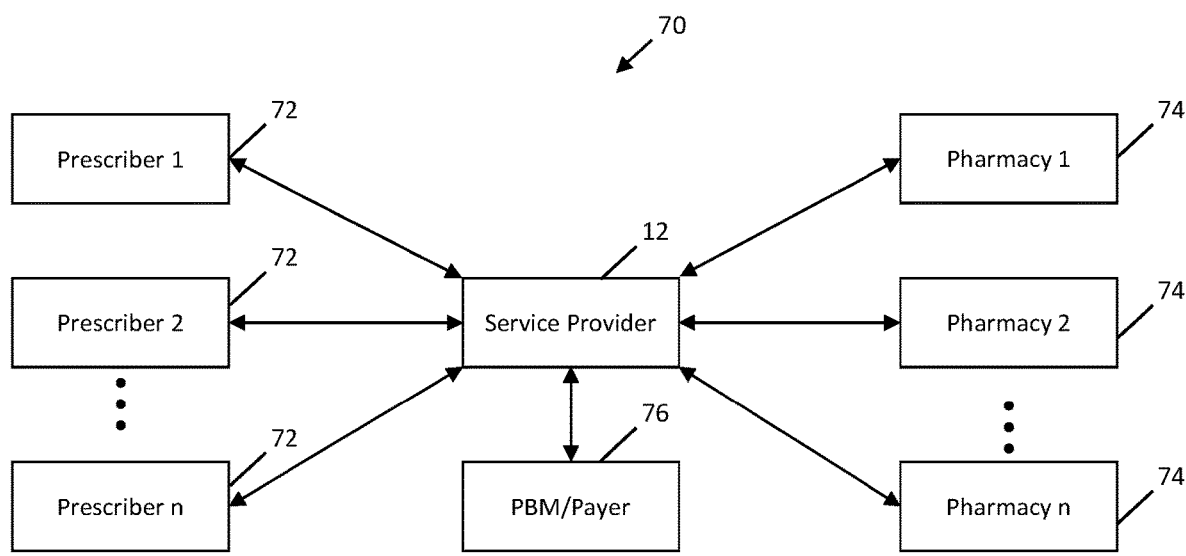
Figure 5A:
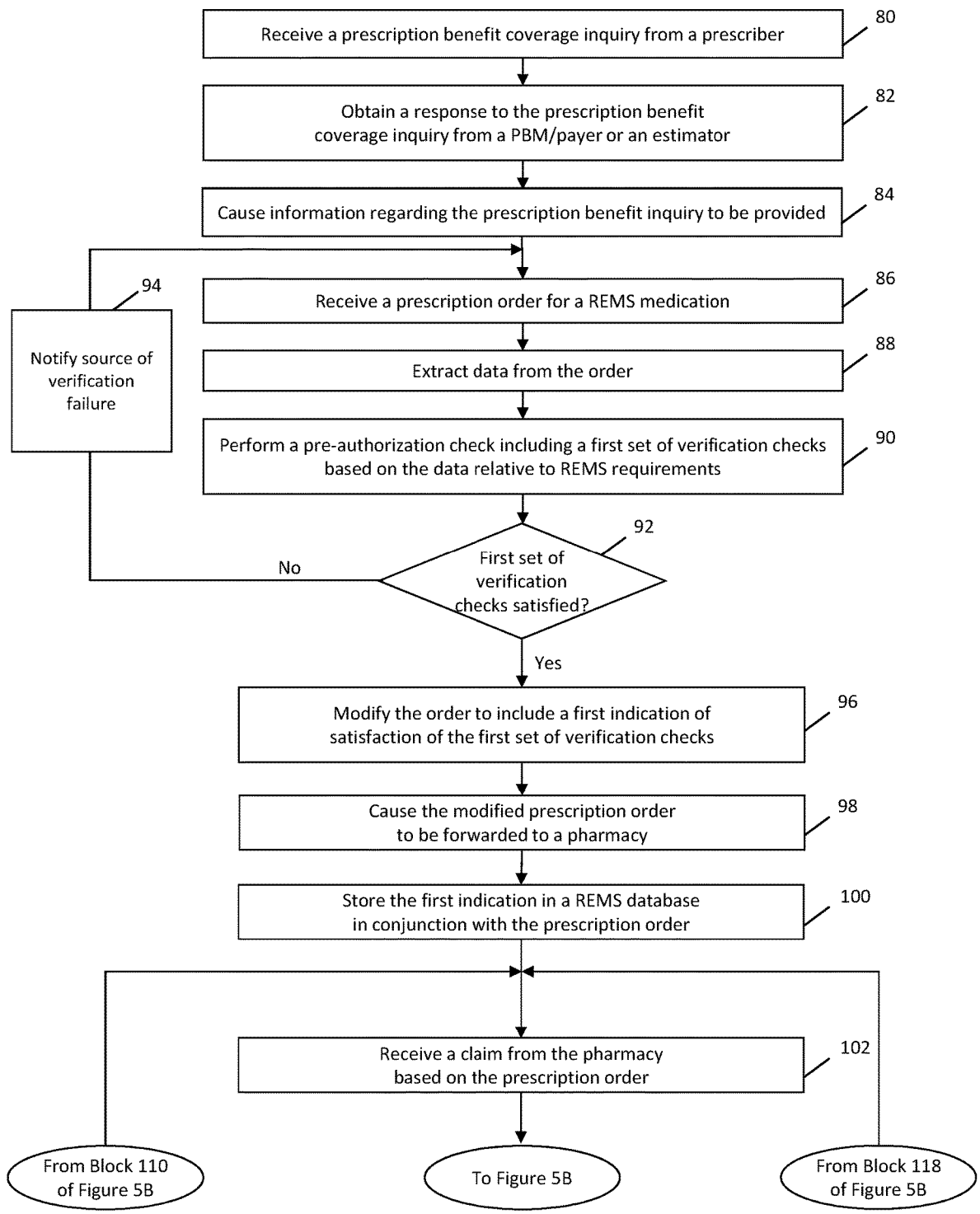
Figure 5B:
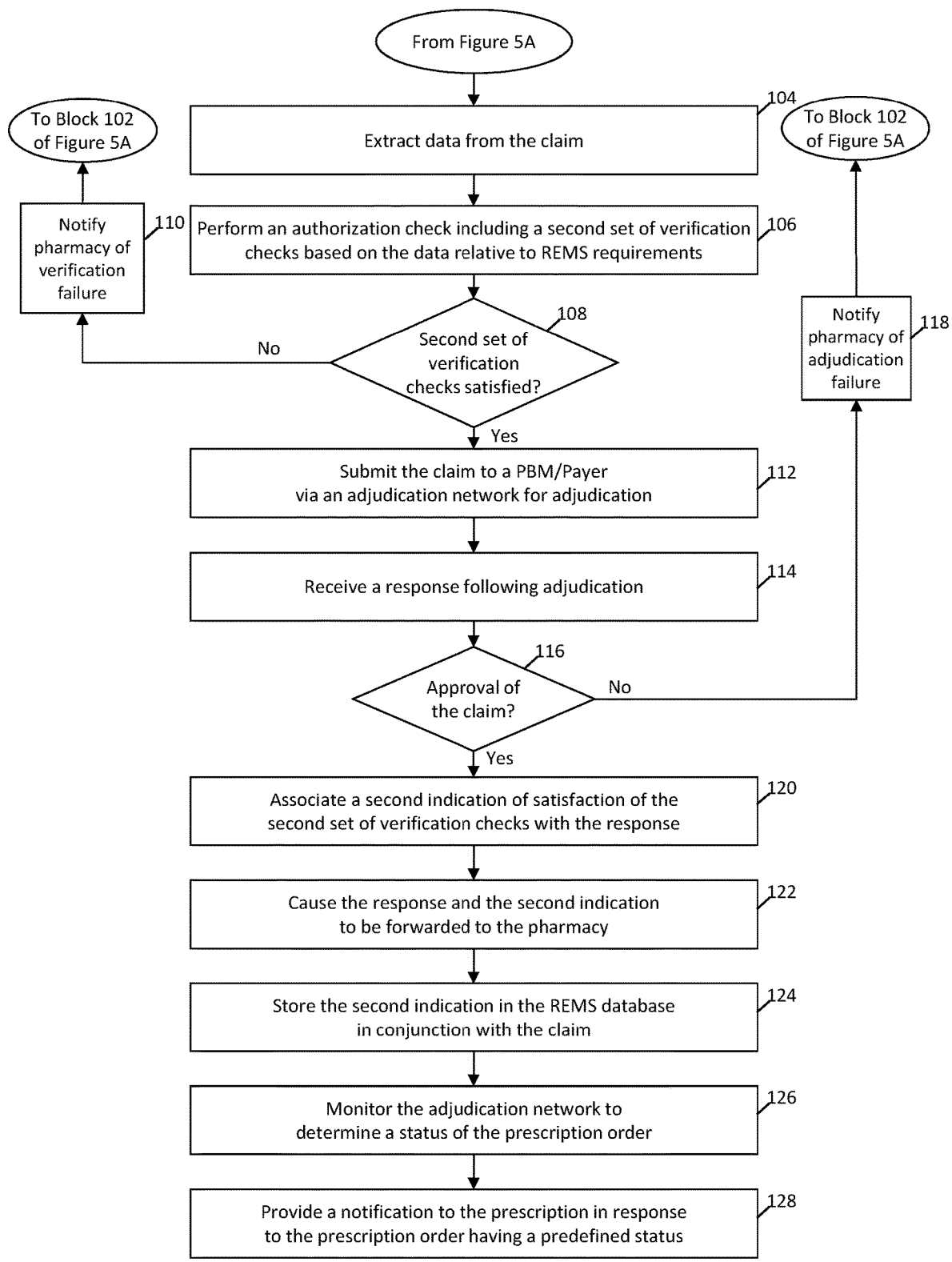
Figure 6:
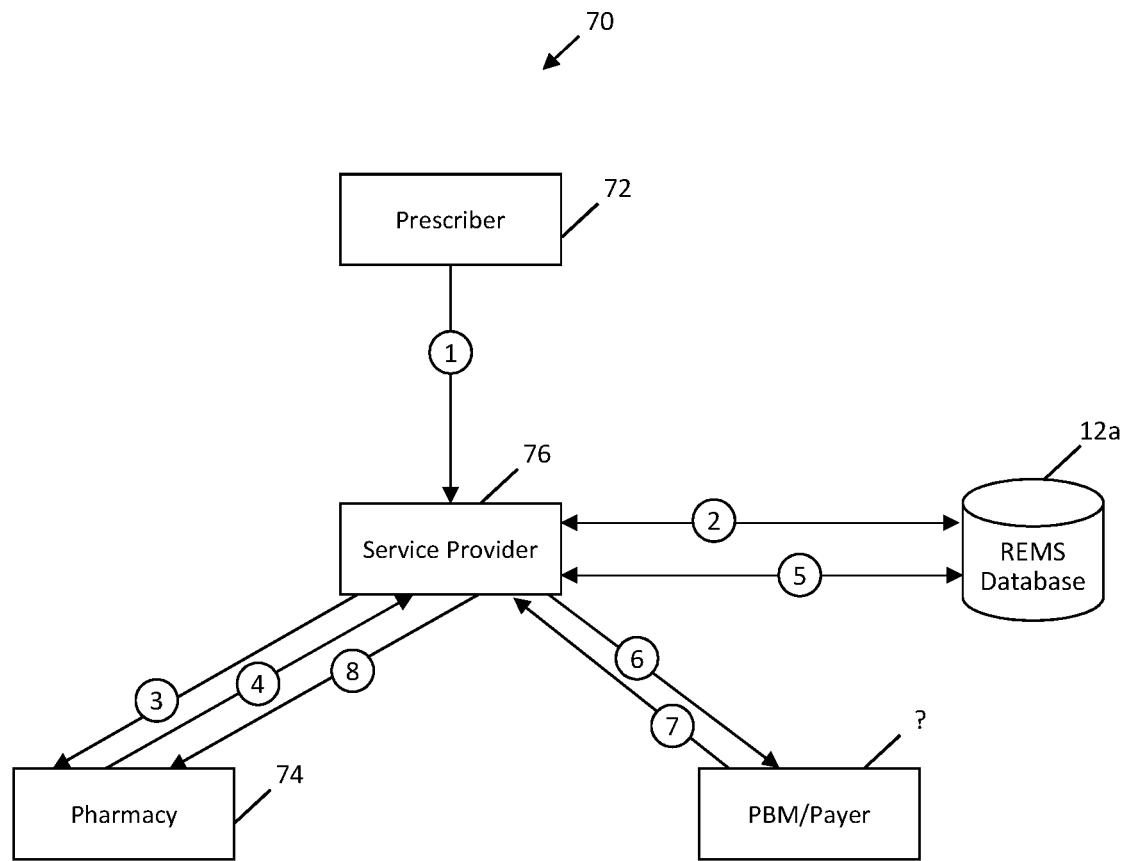
Figure 7A:
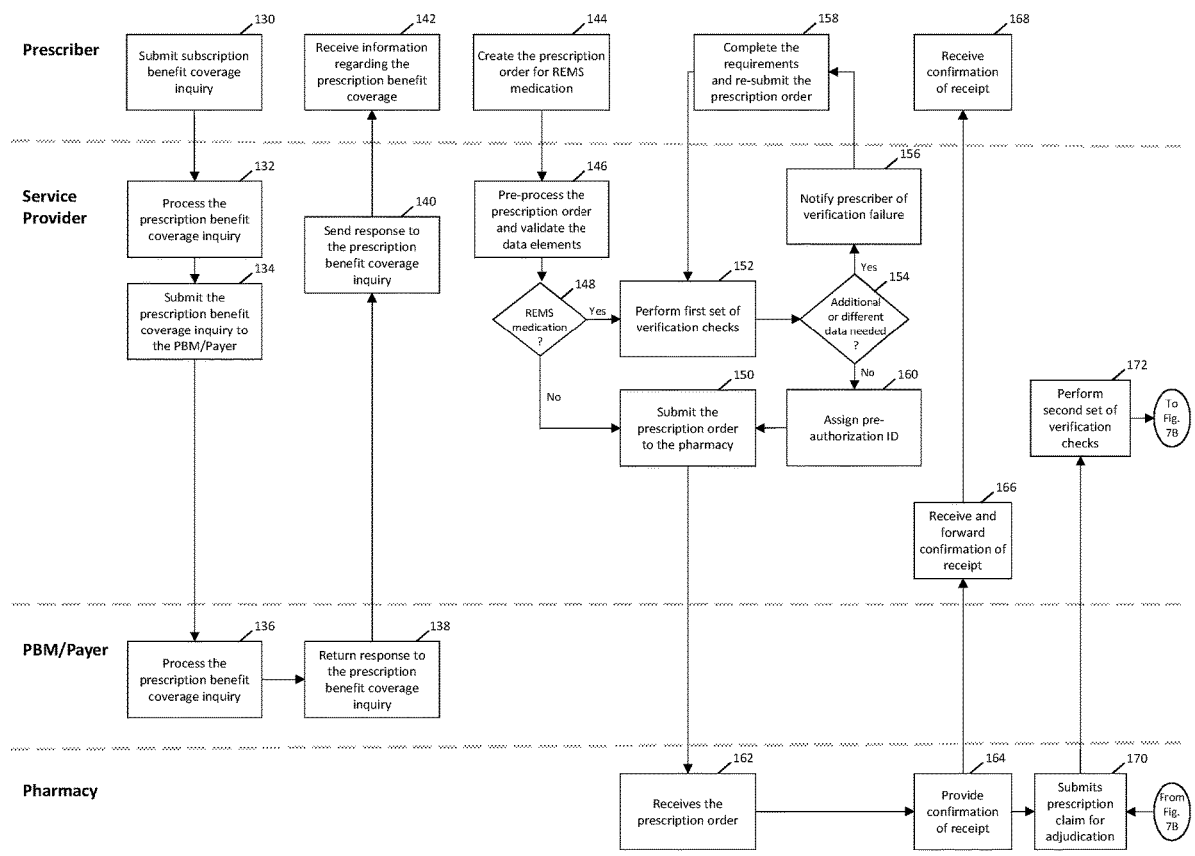
Figure 7B:
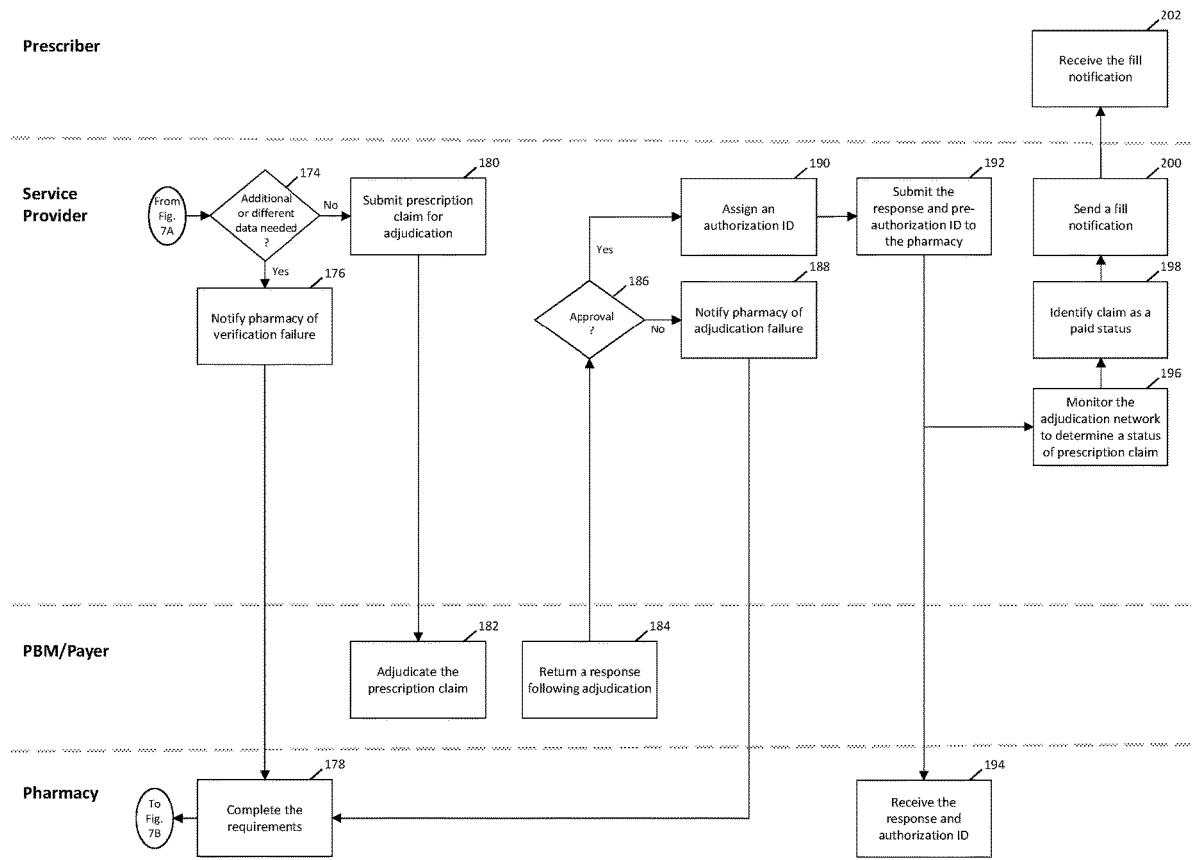

Having thus described certain embodiments of the invention in general terms, reference will now be made to the accompanying drawings, which are not necessarily drawn to scale, and wherein:

FIG. 1 is a block diagram of a system including an apparatus that may be specifically configured in accordance with an example embodiment in order to conduct a multi-stage verification;

FIG. 2 is a block diagram of an apparatus that may be specifically configured in accordance with an example embodiment in order to conduct a multi-stage verification;

FIGS. 3A and 3B are flowcharts of the operations performed, such as by the apparatus of FIG. 2, in accordance with an example embodiment;

FIG. 4 is a block diagram of a system including an apparatus in accordance with an example embodiment in order to facilitate communications between one or more prescribers, one of more pharmacies and one or more pharmacy benefit management entities or payers in order to conduct a multi-stage verification;

FIGS. 5A and 5B are flowcharts illustrating the operations performed, such as by the apparatus of FIG. 2, in accordance with an example embodiment;

FIG. 6 is a block diagram of a system illustrating a sequence of operations performed by a prescriber, a service provider and associated database, a pharmacy and a pharmacy benefit management entity or payer in order to conduct a multi-stage verification; in accordance with an example embodiment; and FIGS. 7A and 7B are a signal flow diagram illustrating the interaction between a prescriber a service provider, a pharmacy benefit management entity or payer and a pharmacy in order to conduct a multi-stage verification in accordance with an example embodiment.

DETAILED DESCRIPTION

The present invention now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

A method, apparatus and computer program product are provided in accordance with an example embodiment in order to conduct a multi-stage verification process. In this regard, in response to receipt of an order submitted pursuant to a program having a plurality of verification qualifications that must be satisfied to qualify the order to be processed and filled in accordance with the program, the method, apparatus and computer program product of an example embodiment are configured to perform at least two different sets of verification checks at different stages of order processing. By performing the multi-stage verification process, the method, apparatus and computer program product of an example embodiment can identify at least some instances in which the order, such as the data from which the order is constructed, fails to satisfy the verification qualifications at an earlier stage in relation to the processing and fulfillment of the order.

As such, the verification failure may be identified and further processing of the order may be halted, thereby conserving computing and network resources that may otherwise be inefficiently consumed with the further processing of an order that will eventually fail to satisfy the verification qualifications of the program according to which the order was submitted. Indeed, in instances in which multiple parties are involved in the processing of an order, the multi-stage verification process employed by the method, apparatus and computer program product of an example embodiment may identify an order that fails to satisfy the verification qualifications of the program with under which the order was submitted at an early enough stage such that further processing of the order is halted before one or more of the parties is ever engaged in the order processing. Further, the multi-stage verification process employed by the method, apparatus and computer program product of an example embodiment also permits the party that submitted order to be notified of the failure to satisfy the verification qualifications of the program under which the order was submitted at an earlier stage, thereby permitting the order to modified and resubmitted with less delay than if the failure of the order to satisfy the verification qualifications was not identified until later in the processing of the order and closer to the fulfillment of the order.

The method, apparatus and computer program product of an example embodiment may be utilized in conjunction with the multi-stage verification of an order in a wide variety of different applications. For example, the method, apparatus and computer program product of an example embodiment may be employed in conjunction with the multi-stage verification of an order submitted in conjunction with a warranty application, an insurance application or a healthcare application, such as in conjunction with the submission and evaluation of an order for a medication pursuant to a Risk Evaluation and Mitigation Strategy (REMS) program and a prescription claim based upon the order.

One example of a system 10 in which the method, apparatus and computer program product of an example embodiment may be deployed is depicted in FIG. 1. As shown, the system includes a service provider 12 that includes or is embodied by the apparatus and is configured to communicate with a plurality of different parties, such as a request processor 14, a source 16 and a fulfillment provider 18. As also shown, the service provider may include or be in communication with a database 12a. The apparatus of the service provider of an example embodiment may, in turn, be embodied by any of variety of different computing devices including, for example, a server, a plurality of networked computing devices, a computer workstation or the like. Regardless of the computing device that embodies the apparatus, the apparatus 20 of the service provider of an example embodiment includes, is associated with or is otherwise in communication with processing circuitry 22, memory 24, communication interface 26 and optionally a user interface 28 as shown, for example, by FIG. 2.

In some embodiments, the processing circuitry 22 (and/or co-processors or any other processors assisting or otherwise associated with the processing circuitry) can be in communication with the memory 24 via a bus for passing information among components of the apparatus 20. The memory can be non-transitory and can include, for example, one or more volatile and/or non-volatile memories. In other words, for example, the memory may be an electronic storage device (for example, a computer readable storage medium) comprising gates configured to store data (for example, bits) that can be retrievable by a machine (for example, a computing device like the processing circuitry). The memory can be configured to store information, data, content, applications, instructions, or the like for enabling the apparatus to carry out various functions in accordance with an example embodiment of the present disclosure. For example, the memory can be configured to buffer input data for processing by the processing circuitry. Additionally or alternatively, the memory can be configured to store instructions for execution by the processing circuitry.

The processing circuitry 22 can be embodied in a number of different ways. For example, the processing circuitry may be embodied as one or more of various hardware processing means such as a processor, a coprocessor, a microprocessor, a controller, a digital signal processor (DSP), a processing element with or without an accompanying DSP, or various other processing circuitry including integrated circuits such as, for example, an ASIC (application specific integrated circuit), an FPGA (field programmable gate array), a microcontroller unit (MCU), a hardware accelerator, a special-purpose computer chip, or the like. As such, in some embodiments, the processing circuitry can include one or more processing cores configured to perform independently. Alternatively, the processing circuitry can include one or more processors configured in tandem via the bus to enable independent execution of instructions.

In an example embodiment, the processing circuitry 22 can be configured to execute instructions stored in the memory 24 or otherwise accessible to the processing circuitry. Alternatively or additionally, the processing circuitry can be configured to execute hard coded functionality. As such, whether configured by hardware or software methods, or by a combination thereof, the processing circuitry can represent an entity (for example, physically embodied in circuitry) capable of performing operations according to an embodiment of the present disclosure while configured accordingly. Thus, for example, when the processing circuitry is embodied as an ASIC, FPGA or the like, the processing circuitry can be specifically configured hardware for conducting the operations described herein. Alternatively, as another example, when the processing circuitry is embodied as an executor of software instructions, the instructions can specifically configure the processing circuitry to perform the algorithms and/or operations described herein when the instructions are executed. However, in some cases, the processing circuitry can be a processor of a specific device (for example, the service provider 12) configured to employ an embodiment of the present disclosure by further configuration of the processor by instructions for performing the algorithms and/or operations described herein. The processing circuitry can include, among other things, a clock, an arithmetic logic unit (ALU) and/or one or more logic gates configured to support operation of the processing circuitry.

The apparatus 20 of an example embodiment can also include the communication interface 26 that can be any means such as a device or circuitry embodied in either hardware or a combination of hardware and software that is configured to receive and/or transmit data from/to other electronic devices in communication with the apparatus, such as a database that stores data generated and/or employed by the processing circuitry 22. Additionally or alternatively, the communication interface can be configured to communicate in accordance with various wireless protocols including Global System for Mobile Communications (GSM), such as but not limited to Long Term Evolution (LTE). In this regard, the communication interface can include, for example, an antenna (or multiple antennas) and supporting hardware and/or software for enabling communications with a wireless communication network. In this regard, the communication interface can include, for example, an antenna (or multiple antennas) and supporting hardware and/or software for enabling communications with a wireless communication network. Additionally or alternatively, the communication interface can include the circuitry for interacting with the antenna(s) to cause transmission of signals via the antenna(s) or to handle receipt of signals received via the antenna(s). In some environments, the communication interface can alternatively or also support wired communication.

The apparatus 10 may also optionally include a user interface 28 that may, in turn, be in communication with the processing circuitry 22 to provide output to a user and, in some embodiments, to receive an indication of a user input. As such, the user interface may include a display and, in some embodiments, may also include a keyboard, a mouse, a joystick, a touch screen, touch areas, soft keys, one or more microphones, a plurality of speakers, or other input/output mechanisms. In one embodiment, the processing circuitry may comprise user interface circuitry configured to control at least some functions of one or more user interface elements such as a display and, in some embodiments, a plurality of speakers, a ringer, one or more microphones and/or the like. The processing circuitry and/or user interface circuitry embodied by the processing circuitry may be configured to control one or more functions of one or more user interface elements through computer program instructions (for example, software and/or firmware) stored on a memory accessible to the processing circuitry (for example, memory 24, and/or the like).

Referring now to FIGS. 3A and 3B, the operations performed, such as by the apparatus 20 of FIG. 2, in accordance with an example embodiment are depicted. As shown in block 30, the apparatus includes means, such as the processing circuitry 22, the communication interface 26 or the like, for receiving an order submitted pursuant to program having a plurality of verification qualifications. The verification qualifications associated with the program must be satisfied in order for the order to be processed and fulfilled in accordance with the program. Once the verification qualifications are satisfied, the program may provide any of a wide variety of different advantages, such as access to the particular product, lower pricing for a product than otherwise available, quicker delivery of the product than otherwise available, etc. In an example embodiment, the service provider 12 is configured to receive the order from a source 16.

The apparatus 20 of an example embodiment is configured to perform an initial check of some of the verification qualifications associated with the program following receipt of the order and prior to further processing of the order, such as by the request processor 14. In this regard, the apparatus includes means, such as the processing circuitry 22 or the like, for extracting data from the order. See block 32. For example, the order may include a plurality of data fields, each of which includes a data element representative of a predefined type of data. The one or more data elements that are extracted from the order include the type(s) of data that are the subject of the initial check of some of the verification qualifications. As such, the apparatus includes means, such as the processing circuitry or the like, for performing a first set of verification checks based upon the data, such as upon one or more of the data elements extracted from the order, and for determining whether the first set of verification checks is satisfied. See blocks 34 and 36. The first set of verification checks may include any of a variety of different types of verification checks, but, in one embodiment, includes the one or more verification checks that are able to be performed based upon the data initially provided with the order without further processing of the order. Thus, the apparatus, such as the processing circuitry, of an example embodiment is configured to determine if the product or service that is the subject of the order and/or if the source 16 of the order satisfy the verification qualifications associated with the program.

In an example embodiment, a database 12a of the service provider 12 or otherwise in communication with the service provider is configured to store information regarding the verification qualifications associated with the program. The apparatus 20, such as the processing circuitry 22, of this example embodiment is configured to compare at least some of the data extracted from the order to information obtained from the database regarding the corresponding verification qualifications of the program so as to determine if the order satisfies this first set of verification checks. For example, the database may include a listing of the products or services that are able to be purchased pursuant to the program and/or a listing of the parties who are registered and/or qualified to submit orders pursuant to the program.

In an instance in which the apparatus 20, such the processing circuitry 22, determines that the first set of verification checks is not satisfied, such as in an instance in which one or more of the data elements extracted from the order differ from and do not satisfy the verification qualifications associated with the program, such as defined by the information stored by the database 12a, the apparatus of an example embodiment includes means, such as the processing circuitry, the communication interface 26 or the like, for notifying the source 16 of the verification failure. See block 38. In this regard, the notification may identify the particular verification qualification(s) that were not satisfied and/or may identify the data element(s) extracted from the order that failed to satisfy the verification qualifications. In some example embodiments, the notification may also provide information regarding how the particular verification qualification(s) can be satisfied, such that the source 16 of the order is better informed in relation to modifying the order to subsequently satisfy the verification qualifications of the program. The source then has the option to modify the order, such as by modifying one or more data elements of the order, in order to satisfy the verification qualifications associated with the program and to then resubmit the order for further evaluation. Alternatively, the source may choose to no longer pursue the order or not to pursue the order pursuant to the program as a result of the failure to satisfy the verification qualifications associated with the program under which the order was previously submitted.

By utilizing a multi-stage verification process and notifying the source 16 if the original order fails to satisfy a first set of verification qualifications without further processing the order, the apparatus 20 of an example embodiment provides for the efficient verification of the order and conserves resources, such as computing and/or network resources, otherwise consumed in conjunction with the processing of the order which subsequently fails to satisfy the verification qualifications. Indeed, the determination that an order fails to satisfy the first set of verification qualifications prior to any processing of the order avoids downstream processing of the order, such as by the fulfillment party 18 as described below, in an instance in which an earlier stage of the verification process indicates that the order will fail to satisfy the verification qualifications. In this example embodiment, the fulfillment party will not be required to expend computing resources with respect to the processing of the order in an instance in which this earlier stage in the verification process indicates that the order will fail to satisfy the verification qualifications.

However, as shown in block 40, in an instance in which the first set of verification checks is satisfied, the apparatus 20 of an example embodiment includes means, such as the processing circuitry 22 or the like, for modifying the order to include a first indication of the satisfaction of the first set of verification checks. In this regard, the order may include a data field that was not previously utilized, but that may now be populated with the first indication, such as a pre-authorization identifier (ID) that is generated by the service provider 12. The apparatus of this example embodiment also includes means, such the processing circuitry, the communications interface 26 or the like, for causing the order, as modified to include the first indication, to be provided to the fulfillment party 18. In this regard, the service provider may be configured to provide the order, as modified, directly to the fulfillment part or the service provider may be configured to return the order, as modified, to the source 16 which, in turn, submits the order to the fulfillment party. Upon receipt of the order, as modified, the fulfillment party provides the product or service that is the subject to the order once the remainder of the verification qualifications associated with the program are satisfied. Prior to providing the product or service, however, the fulfillment party submits a claim that is directed via the service provider to the request processor 14, such as to seek payment, in whole or in part, for the product or service to be provided by the fulfillment party.

As such, the apparatus 20 of this example embodiment includes means, such as the processing circuitry 22, the communication interface 26 or the like, for receiving a claim from the fulfillment provider 18 based on the order. See block 42. Upon receipt of the claim, the apparatus, such as the processing circuitry, is configured to perform a second set of verification checks in order to determine if the claim satisfies all of the verification qualifications associated with the program under which the order was submitted. In this regard, the second set of verification checks may include checks for different verification qualifications than those that were checked during the first set of verification checks and optionally a recheck of one or more of the verification qualifications that were previously checked as part of the first set of verification checks. In an example embodiment, each of the checks of the verification qualifications must be satisfied prior to filling the order, such as by dispensing the medication.

In this regard, the apparatus 20 includes means, such as the processing circuitry 22 or the like, for extracting data from the claim. See block 44. Like the order, the claim may include a plurality of data fields, each of which includes a data element representative of a predefined type of data. The one or more data elements that are extracted from the claim include the type(s) of data that are the subject of the second check of the verification qualifications. As such, the apparatus includes means, such as the processing circuitry or the like, for performing the second set of verification checks based upon the data, such as upon one or more of the data elements extracted from the claim, and for determining whether the second set of verification checks is satisfied. See blocks 46 and 48. As described above, the apparatus, such as the processing circuitry, of this example embodiment may also be configured to compare at least some of the data extracted from the claim to information obtained from the database 12a associated with the service provider 12 regarding the corresponding verification qualifications of the program so as to determine if the claim satisfies the second set of verification checks.

In this example embodiment, the combination of the first and second sets of verification checks fully determine whether the verification qualifications associated with the program under which the order and claim were submitted are satisfied and, as such, determine whether the order and the claim can be satisfied pursuant to the program. In this regard, while the first set of verification qualifications may be limited to those that can be checked based upon the data associated with the order itself, the second set of verification qualifications may include the evaluation of data from the claim that was not provided with the original order, but that is the product of processing of the order and/or that has otherwise been added, such as by the service provider 12, the source 16 or the fulfillment party 18, following the initial submission of the order.

In an instance in which the apparatus 20, such the processing circuitry 22, determines that the second set of verification checks is not satisfied, such as in an instance in which one or more of the data elements extracted from the claim differ from and do not satisfy the verification qualifications associated with the program, such as defined by the information stored by the database 12a, the apparatus of an example embodiment includes means, such as the processing circuitry, the communication interface 26 or the like, for notifying the fulfillment party 18 of the verification failure. See block 50. In this regard, the notification may identify the particular verification qualification(s) that were not satisfied and/or may identify the data element(s) extracted from the claim that failed to satisfy the verification qualifications. In some example embodiments, the notification may also provide information regarding how the particular verification qualification(s) can be satisfied, such that the fulfillment party is better informed in relation to modifying the claim to subsequently satisfy the verification qualifications of the program. The fulfillment party then has the option to modify the claim, such as by modifying one or more data elements of the claim, in order to satisfy the verification qualifications associated with the program and to then resubmit the claim for further evaluation. Alternatively, the fulfillment party may choose to no longer pursue the claim, such as by not providing the product or service that is the subject of the order, by not seeking at least partial payment by the request processor 16 or by providing he product or service outside of the program as a result of the failure to satisfy the verification qualifications associated with the program under which the order and claim were previously submitted. In either instance, each of the checks of the verification qualifications must be satisfied before the fulfillment party fills the order, such as by dispensing the medication.

In an instance in which the second set of verification checks are satisfied, however, the apparatus 20 includes means, such as the processing circuitry 22, the communication interface 26 or the like, for causing the claim to be submitted via an adjudication network for adjudication, such as by the request processor 16. See block 52. Following the adjudication, the apparatus includes means, such as the processing circuitry, the communication interface or the like, for receiving a response, such as from the request processor, and for determining whether the response approves of the claim. See blocks 54 and 56. In this regard, the response may indicate that the claim has been approved, such as in an instance in which the request processor indicates that the product or service that is the subject of the order with which the claim is associated will be paid, either entirely or at least partially, by a third-party payor. Alternatively, the response may indicate that the claim has been disapproved, such as in an instance in which the product or service that is the subject of the order with which the claim is associated will not be paid by a third-party payor.

In an instance in which the response indicates that the claim has not been approved for payment, the apparatus 20 of an example embodiment includes means, such as the processing circuitry 22, the communication interface 26 or the like, for notifying the fulfillment party 18 of the adjudication failure. See block 58. In this regard, the notification may identify the reason(s) as why the claim was not approved, if the response from the request processor 16 provides the reason(s). The fulfillment party then has the option to modify the claim, such as by modifying one or more data elements of the claim, in order to address the reason(s) for the prior disapproval of the claim and to then resubmit the claim for further evaluation. Alternatively, the fulfillment party may choose to no longer pursue the claim, such as by not providing the product or service that is the subject of the order or by not seeking at least partial payment by the request processor.

However, in an instance in which the response indicates that the claim has been approved, the apparatus 20 includes means, such as the processing circuitry 22 or the like, for generating a second indication of the satisfaction of the second set of verification checks, such as an authorization ID. The apparatus of this example embodiment includes means, such as the processing circuitry or the like, for associating the second indication with the response. See block 60. The second indication may be associated with the response in various manners. In one embodiment, however, the apparatus, such as the processing circuitry, is configured to modify the response so as to include the authorization ID, thereby serving to indicate that the second set of verification checks has been satisfied. In this regard, the response may include a data field that was not previously utilized, but that may now be populated with the second indication, such as the authorization ID that is generated by the service provider 12.

The apparatus 20 of this example embodiment also includes means, such as the processing circuitry 22, the communications interface 26 or the like, for causing the response including the associated second indication, such as the authorization ID, to be provided to the fulfillment party 18. The fulfillment party may then fulfill the order from the source 16, such as by providing the product of service that was the subject of the order to the source or other recipient.

In accordance with an example embodiment described above in which the fulfillment party 18 that receives the order looks to a different party, such as the request processor 14, for at least a portion of the payment for the one or more products or services that are the subject of the order, the apparatus 20 includes means, such as the processing circuitry 22 or the like, for monitoring the adjudication network established by or with the request processor in order to monitor the status of the order, after the response including the second indication has been provided to the fulfillment party. See block 62. In this regard, after receipt of the order, the product or service that is the subject of the order may not be provided by the fulfillment party to the source 16 or other recipient for some time, if at all, such as in an instance in which the recipient fails to pick up the product from the fulfillment party.

By monitoring the adjudication network, the apparatus 20, such as the processing circuitry 22, is configured to identify an instance in which the status of the order changes from a final claim status that was established upon the fulfillment party 18 being provided with the response and the second indication, such as the authorization ID. In this regard, the apparatus, such as the processing circuitry or the like, is configured to identify the change in status of the order, such as to a paid status, and to correlate the change in status to the provision of the product or service that is the subject of the order by the fulfillment party to the source 16 or other recipient. Thus, the apparatus of this example embodiment may include means, such as the processing circuitry, the communication interface 26 or the like, for providing a notification to the source that submitted the order in response to the order having a predetermined status, such as a paid status, that is indicative of the order having been provided to the source or other recipient. See block 64.

As a result of monitoring the adjudication network and providing a notification in an instance in which the order has a predetermined status, the source 16 that submitted the order is assured of receiving feedback in an instance in which the order is provided to the recipient. In this regard, the apparatus 20, such as the processing circuitry 22, the communication interface 26 or the like, may be configured to monitor the adjudication network for a predefined period of time. Thus, the source is assured of receiving a response regarding the status of the order within the predefined period of time, such as an indication that the product or service that is the subject of the order has been provided to the recipient or that the product or service that is the subject of the order has not been provided to the recipient (in an instance in which the predefined period of time expires without a change in the order status). Consequently, the source has less incentive to resubmit the order out of concern that the initial order was misdirected or otherwise not successfully received and processed and correspondingly reduces the burden upon the communication network and/or the computing devices of the various parties relative to instances in which the source resubmits the order.

As noted above, the method, apparatus 20 and computer program product of an example embodiment may be utilized in a wide variety of different applications. By way of example, but not of limitation, the method, apparatus and computer program product of an example embodiment are described hereinafter in relation to FIGS. 4-7 in the context of a healthcare application, such as in conjunction with the submission and evaluation of an order for a medication pursuant to a REMS program and a prescription claim based upon the order. REMS is a drug safety program required by the Food and Drug Administration (FDA) to ensure safe distribution of select medications to consumers. Specifically, a REMS program may be enforced for select medications, such as certain medications identified as a potential high-risk to consumers. Implementing a REMS program may include implementing specifically designated precautions that may reduce the risk of the medication to consumers. Thus, the REMS program is subject to a plurality of verification qualifications in terms of the medication, the prescriber prescribing the medication, the pharmacy dispensing the medication, the patient being prescribed the medication and others, all of which must be satisfied for a prescription to be successfully processed pursuant to the REMS program.

In this regard, a REMS program, for example, may include requiring specialty training and/or certification for any healthcare provider who prescribes and/or dispenses a particular medication. Other REMS programs may require registration by the patient in a registry so that the patient may be monitored or easily identified in the future. As another example, in order to receive a particular medication, some REMS programs may require a laboratory test be taken by the recipient of the medication prior to receiving the medication. For example, some medications known to cause birth defects, may be subject to a REMS program requiring the patient take a pregnancy test prior to receiving the medication.

As shown in FIG. 4, a system 70 includes a service provider 12 which, in turn, includes an apparatus 20 as shown in FIG. 2 and described above. Although not shown in FIG. 4, the service provider may also include or otherwise be associated with or in communication with a database 12a that stores information regarding the program under which an order is submitted including, for example, the verification qualifications. The system of FIG. 4 also includes one or more sources in the form of one or more prescribers 72 designated as Prescriber 1, Prescriber 2, . . . . Prescriber n in FIG. 4. A prescriber is a healthcare professional, such as a physician or other healthcare practitioner or practice or a healthcare system, such as an electronic healthcare record system operated or otherwise utilized by a physician or other healthcare practitioner to write and submit prescriptions for patients. Further, the system of this example embodiment includes one or more fulfillment parties in the form of one or more pharmacies 74 designated as Pharmacy 1, Pharmacy 2, . . . Pharmacy n in the example embodiment of FIG. 4. These pharmacies may be brick and mortar pharmacies or may be online or other types of pharmacies that fill prescription orders. The system of this example embodiment also includes one or more request processors in the form of a pharmacy benefit management (PBM) entity or other payer, such as an insurance company or the like. Although FIG. 4 depicts a single request processor in the form of a PBM/Payer 76, the system of this example embodiment may, instead, include a plurality of PBMs/payers. As described below, the pharmacies are configured to communicate with the PBMs or other payers to provide at least partial payment for the prescription orders.

As shown in block 80 of FIG. 5A, the apparatus 20 embodied by the service processor 12 in accordance with an example embodiment includes means, such as the processing circuitry 22, the communication interface 26 or the like, for receiving a prescription benefit coverage inquiry from a prescriber 72. The prescription benefit coverage inquiry is submitted by the prescriber as shown in block 130 of FIG. 7A and identifies a particular medication or other item that may subsequently be the subject of a prescription order and may solicit information regarding the amount that a PBM or other payer 76 would pay on behalf of the patient in an instance in which the patient were to fill a prescription for the medication or other item.

Thus, the apparatus 20 is configured to determine the amount that the PBM or other payer 76 would pay on behalf of the patient once a prescription for the medication or other item identified by the prescription benefit coverage inquiry has been filled. This determination of the coverage amount may be performed in various manners. In one embodiment, the apparatus determines the coverage amount based on information provided by the PBM or other payer. As such, the apparatus, such as the processing circuitry 22, the communication interface 26 or the like, may be configured to process the prescription benefit coverage inquiry and to transmit the prescription benefit coverage inquiry or at least information provided by the prescription benefit coverage inquiry, to the PBM or other payer. See blocks 132 and 134 of FIG. 7A. In this regard, the prescription benefit coverage inquiry may identify the respective PBM or other payer to which the prescription benefit coverage inquiry is directed such that the apparatus and, more particularly, the processing circuitry or the communication interface may be configured to identify the respective PBM or other payer to which the prescription benefit coverage inquiry is to be directed and then correspondingly provide the prescription benefit coverage inquiry or at least information provided by and related to the prescription benefit coverage inquiry to the respective PBM or other payer.

As shown in block 82, the apparatus 20 of this example embodiment also includes means, such as the processing circuitry 22, the communication interface 26 or the like, for obtaining a response to the prescription benefit coverage inquiry from the respective PBM or other payer 76. As shown in blocks 136 and 138 of FIG. 7A, the PBM/payer processes the prescription benefit coverage inquiry and then returns the response. The response identifies the amount that the PBM or other payer would pay on behalf of the patient once a prescription for the medication or other item identified by the prescription benefit coverage inquiry has been filled.

In other embodiments, the apparatus 20 does not determine the coverage amount based on information provided by the PBM or other payer 76, but, instead, estimates the coverage amount, such as based on historical information. In this example embodiment, the apparatus includes means, such as the processing circuitry 22, the memory 24 or the like, for determining an estimate of the amount that a PBM or other payer would pay on behalf of the patient for a particular medication or other item. For example, the apparatus, such as the memory, database 12a or another database with which the apparatus is in communication, may store historical information regarding the amount that a respective PBM or other payer has paid in the past for the same or similar quantity of the same medication having the same National Drug Code (NDC) pursuant to the REMS program. In some embodiments, the historical information that is considered is also limited to historical information for the same pharmacy or chain of pharmacies in the same state. Further, the historical information that is considered may be limited to a most recent time period, such as an immediately preceding 60 day period. Based upon the historical information, the apparatus, such as the processing circuitry, is configured to determine the estimated amount that will be paid by the PBM or other payer.

In order to increase the confidence in the estimated amount, the apparatus 20, such as the processing circuitry 22, may be configured to require the historical amounts that the respective PBM or other payer has paid in the past to be within a predefined range, such as $10. In an instance in which the historical amounts that the respective PBM or other payer has paid in the past are not within the predefined range, the apparatus, such as the processing circuitry, may be configured to indicate that an estimated amount cannot be determined. However, in an instance in which the historical amounts that the respective PBM or other payer has paid in the past are within the predefined range, the apparatus, such as the processing circuitry, may be configured to determine an estimated amount in the form of a range of historical amounts paid by the PBM or other payer for the same or a similar quantity of the same medication having the same NDC pursuant to the REMS program. In some embodiments, any outlying historical amounts may be removed from consideration prior to determining the range of historical amounts. For example, the apparatus, such as the processing circuitry, may be configured to construct a distribution of the historical amounts and to then define the range of the historical amounts that will form the estimated amount to be within a predefined range of the mean of the distribution, such as within one or a predefined number, e.g., 2, of standard deviations of the mean.

The apparatus 20, such as the processing circuitry 22, may be configured to determine whether to provide the response to the prescription benefit coverage inquiry based upon the information provided by a PBM or other respective payer 76 or based upon an estimate that relies upon historical information in various manners. For example, the apparatus, such as the processing circuitry, may be configured to initially attempt to obtain the coverage amount from the respective PBM or other payer and to only determine an estimate of the coverage amount based upon historical information in an instance in which the coverage amount cannot be obtained from the respective PBM or other payer, such as an instance in which the respective PBM or other payer does not respond or in an instance in which the prescription benefit coverage inquiry does not identify a respective PBM or other payer and/or does not provide the necessary eligibility data for the patient. Alternatively, the apparatus, such as the processing circuitry, may be configured to initially determine an estimate of the coverage amount based upon historical information in an instance in which both the prescription benefit coverage inquiry provided sufficient information to allow for such an estimate and in which sufficient historical information is accessible to allow the estimate to be performed. In this example embodiment in which there is an initial attempt to estimate the coverage amount, the apparatus, such as the processing circuitry, the communication interface 26 or the like, is configured to only solicit a response from the respective PBM or other payer in an instance in which an estimated amount cannot be determined. Thus, the apparatus of this example embodiment limits communication with the PBM or other payer, thereby conserving network resources that would otherwise be consumed for the communications with the respective PBM or other payer and also conserving computing resources of the respective PBM or other payer.

Regardless of the manner in which the response to the prescription benefit coverage inquiry is determined, the apparatus 20 includes means, such as the processing circuitry 22, the communication interface 26 or the like, for causing information regarding the prescription benefit coverage to be provided to the prescriber 72 as shown in block 84 of FIG. 5A. See also blocks 140 and 142 of FIG. 7A.

The apparatus 20 of this example embodiment also includes means, such the processing circuitry 22, the communication interface 26 or the like, for thereafter receiving a prescription order from the prescriber 72. See block 86 of FIG. 5A and operation 1 of FIG. 6. In this regard, the prescription order that is created by the prescriber as shown in block 144 of FIG. 7A may be based at least in part upon the information that has been provided regarding the prescription benefit coverage. For example, the prescriber and/or the patient may determine that a prescription order is to be placed for the medication or other item pursuant to the REMS program in an instance in which the prescription benefit coverage will be sufficient to permit the patient to afford the medication or other item. The prescription order may include clinical information, such as the name, the quantity, the days supply and the strength of a drug to be dispensed and/or the name and strength of each ingredient to be compounded. In some embodiments, the clinical information included in the prescription order is defined by the standard, such as the National Council for Prescription Drug Programs (NCPDP) SCRIPT standard, that governs the information that must be included in the order that is submitted to the pharmacy. In addition, the prescription order is generally formatted in accordance with a predefined format, such as an application programming interface (API) format to which the parties agree in advance or a Health Level 7 (HL7) format that is commonly utilized by prescribers and the electronic healthcare record systems employed by prescribers in conjunction with this submission of prescription order.

In order to avoid the consumption of network resources and the computing resources of the pharmacies 74 and PBMs or other payers 76 in relation to a prescription order that is incomplete, the apparatus 20 of an example embodiment includes means, such as the processing circuitry 22 or the like, for pre-processing the prescription order to determine whether all necessary data elements of the prescription order have been provided. See block block 146 of FIG. 7A in which the data elements are validated. In this regard, the apparatus, such as the memory 24 or a database with which the apparatus is in communication, may include information defining the necessary data elements for a prescription order or the necessary data elements for certain types of prescription orders, such as the data elements required of a prescription order submitted pursuant to the REMS program and/or the data elements defined by the standard, e.g., the NCPDP SCRIPT standard, that governs the information that must be included in the order that is submitted to the pharmacy. In an instance in which the prescription order is determined not to include all necessary data elements, the apparatus, such as the processing circuitry, is configured to further process the prescription order in an effort to supplement the prescription order with one or more additional data elements that are required, but that are not currently included in the prescription order.

The one or more additional data elements may be obtained in various manners. For example, the apparatus 20 may include means, such as the processing circuitry 22, the communication interface 26 or the like, for communicating with the prescriber 72 to obtain the one or more additional data elements with which to supplement the prescription order. In this regard, the apparatus, such as the processing circuitry, the communication interface or the like, is configured to transmit a message to the prescriber identifying the one or more data elements that should be provided, but that were not included in the prescription order and to request that the prescriber provide the one or more additional elements.

In an instance in which the one or more additional data elements that are not included in the prescription order are not provided by the prescriber 72, the prescription order cannot be properly processed and the apparatus 20, such as the processing circuitry 22, the communication interface 26 or the like, is configured to notify the prescriber of the failure to process the prescription order and may request that the prescriber subsequently submit a prescription order including all required data fields if the prescriber desires for the prescription order to be properly processed.

However, in an instance in which the prescription order submitted by the prescriber 72 is complete and includes all required data elements or in an instance in which one or more necessary data elements are missing from the prescription order, but are subsequently provided by reference to historical information or to additional information provided by the prescriber in order to complete the prescription order, the apparatus 20 of an example embodiment includes means, such as the processing circuitry 22 or the like, for extracting data from the order. See block 88 of FIG. 5A. In this regard, the order may include a plurality of data fields, each of which includes a data element of a predefined type. Among the data elements extracted from the order in one embodiment is a data element that indicates if the prescription order is being submitted pursuant to a REMS program such that the apparatus, such as the processing circuitry 22, is able to determine whether the prescription order relates to a REMS medication, that is, a medication that is able to be provided pursuant to the REMS program. See block 148 of FIG. 7A. If the prescription order does not relate to a REMS medication, the order may be submitted to the pharmacy 74 as shown in block 150 of FIG. 7B.

If, however, the prescription order does relate to a REMS medication, the apparatus 20 of an example embodiment includes means, such as the processing circuitry 22 or the like, for performing a first check of verification checks, that is, a pre-authorization check as shown by operation 2 of FIG. 6, based on the data extracted from the prescription order, such as based upon one or more of the data elements extracted from the order, relative to the REMS requirements and for determining whether the first set of verification checks is satisfied. See blocks 90 and 92 of FIG. 5A and block 152 of FIG. 7A. The first set of verification checks may include any of a variety of different types of verification checks, but, in one embodiment, includes one or more verification checks that are able to be performed based upon the data initially provided with the prescription order without further processing of the prescription order. For example, the apparatus, such as the processing circuitry, of an example embodiment is configured to determine whether the medication as defined by an NDC is a medication that may be provided pursuant to the REMS program, whether the patient, the prescriber 72 and/or the pharmacy 74 are enrolled or otherwise participate in the REMS program, whether any laboratory reports necessary for participation in the REMS program have been completed, etc. Thus, the apparatus, such as the processing circuitry, of an example embodiment is configured to determine if the prescription order satisfies these initial verification qualifications associated with the REMS program.

In an example embodiment, a database 12a of the service provider 12 or otherwise in communication with the service provider is configured to store information regarding the verification qualifications associated with the REMS program. The apparatus 20, such as the processing circuitry 22, of this example embodiment is configured to compare at least some of the data extracted from the prescription order to information obtained from the database regarding the corresponding verification qualifications of the program so as to determine if the prescription order satisfies this first set of verification checks. For example, the database may include a listing of the NDC numbers of medication that is able to be purchased pursuant to the REMS program and/or a listing of the patients, prescribers 72 and pharmacies 74 who are enrolled in the REMS program.

In an instance in which the apparatus 20, such the processing circuitry 22, determines that the first set of verification checks is not satisfied, such as in an instance in which one or more of the data elements extracted from the order differ from and do not satisfy the verification qualifications associated with the REMS program, such as defined by the information stored by the database 12a, the apparatus of an example embodiment includes means, such as the processing circuitry, the communication interface 26 or the like, for notifying the prescriber 72 of the verification failure. See block 94 of FIG. 5A and blocks 154 and 156 of FIG. 7A. In this regard, the notification may identify the particular verification qualification(s) that were not satisfied and/or may identify the data element(s) extracted from the order that failed to satisfy the verification qualifications. In some example embodiments, the notification may also provide information regarding how the particular verification qualification(s) can be satisfied, such that the prescriber is better informed in relation to modifying the prescription order to subsequently satisfy the verification qualifications of the REMS program. The prescriber then has the prescription option to modify the order, such as by modifying one or more data elements of the order, in order to satisfy the verification qualifications associated with the REMS program and to then resubmit the order for further evaluation. See block 158 of FIG. 7A. Alternatively, the prescriber may choose to no longer pursue the prescription order or not to pursue the order pursuant to the REMS program as a result of the failure to satisfy the verification qualifications associated with the REMS program under which the order was previously submitted.

By utilizing a multi-stage verification process and notifying the prescriber 72 if the original prescription order fails to satisfy a first set of verification qualifications without further processing the order, the apparatus 20 of an example embodiment provides for the efficient verification of the prescription order and conserves resources, such as computing and/or network resources, otherwise consumed in conjunction with the processing of the order which subsequently fails to satisfy the verification qualifications. Indeed, the determination that a prescription order fails to satisfy the first set of verification qualifications prior to any processing of the order avoids downstream processing of the order, such as by the pharmacy 74 as described below, in an instance in which an earlier stage of the verification process indicates that the prescription order will fail to satisfy the verification qualifications. In this example embodiment, the pharmacy 74 will not be required to expend computing resources with respect to the processing of the prescription order in an instance in which this earlier stage in the verification process indicates that the order will fail to satisfy the verification qualifications.

However, as shown in block 96 of FIG. 5A, in an instance in which the first set of verification checks is satisfied, the apparatus 20 of an example embodiment includes means, such as the processing circuitry 22 or the like, for modifying the prescription order to include a first indication of the satisfaction of the first set of verification checks. The first indication may be a pre-authorization ID that is assigned to the prescription order as shown in block 160 of FIG. 7A. In this regard, the prescription order may include a data field that was not previously utilized, but that may now be populated with the first indication, such as the pre-authorization identifier (ID) that is generated by the service provider 12. The apparatus of this example embodiment also includes means, such the processing circuitry, the communications interface 26 or the like, for causing the prescription order, as modified to include the first indication, to be provided to the pharmacy 74. See block 98 of FIG. 5A, operation 3 of FIG. 6 and block 150 of FIG. 7A. In this regard, the service provider may be configured to provide the order, as modified, directly to the pharmacy or the service provider may be configured to return the order, as modified, to the prescriber 72 which, in turn, submits the order to the pharmacy. In addition, the apparatus, such as the processing circuitry, the memory 24 or the like, of an example embodiment is configured to store the first indication, such as the pre-authorization ID, such as in the database 12*a*, in association with the prescription order. See block 100 of FIG. 5A. The first indication, such as the pre-authorization ID, may be stored for various purposes including tracking and/or logging purposes.

Upon receipt of the prescription order, as modified, as shown in block 162 of FIG. 7A, the pharmacy 74 confirms receipt of the order as shown by blocks 164, 166 and 168 of FIG. 7A. The pharmacy then processes the order and provides the medication that is the subject to the prescription order once the remainder of the verification qualifications associated with the REMS program are satisfied. Prior to providing the medication, however, the pharmacy 74 submits a prescription claim that is directed via the service provider 12 to the PBM/Payer 76 for adjudication, such as to seek payment, in whole or in part, for the medication to be provided by the pharmacy. See block 170 of FIG. 7A.

As such, the apparatus 20 of this example embodiment includes means, such as the processing circuitry 22, the communication interface 26 or the like, for receiving a prescription claim from the pharmacy 74 based on the order. See block 102 of FIG. 5A and operation 4 of FIG. 6. Upon receipt of the prescription claim, the apparatus, such as the processing circuitry, is configured to extract data from the claim. See block 104 of FIG. 5B. In this regard, the prescription claim may include a plurality of data fields, each of which includes a data element of a predefined type.

Based upon at least some of the data extracted from the prescription claim, the apparatus 20 includes means, such as the processing circuitry 22 or the like, for performing a second set of verification checks in order to determine if the claim satisfies all of the verification qualifications associated with the REMS program under which the prescription order was submitted. See blocks 106 and 108 of FIG. 5B, operation 5 of FIG. 6 and block 172 of FIG. 7A. In this regard, the second set of verification checks may include checks for different verification qualifications than those that were checked during the first set of verification checks, such as one or more verification checks of information included in or associated with the claim that was not included in or associated with the order. The one or more verification checks of the second set of verification checks that are different than the first set of verification checks may include, for example, one or more verification checks of action taken in response to the order and/or one or more verification checks that are dependent upon a timing associated with the order. For example, the second set of checks may include a check to determine whether the time elapsed from when the prescription was written to when the prescription was filled satisfies the requirements for the REMS program, As another example, the second set of checks may include a verification of validity of the first set of verification checks, such as to determine whether the first indication, e.g., the pre-authorization ID, is valid. Optionally, the second set of verification checks may include one or more verification checks that were also included in the first set of verification checks. As described above, the apparatus 20, such as the processing circuitry 22, of this example embodiment may also be configured to compare at least some of the data extracted from the prescription claim to information obtained from the database 12*a* associated with the service provider 12 regarding the corresponding verification qualifications of the REMS program so as to determine if the claim satisfies the second set of verification checks.

In this example embodiment, the combination of the first and second sets of verification checks fully determine whether the verification qualifications associated with the REMS program under which the prescription order and claim were submitted are satisfied and, as such, determine whether the order and the claim can be satisfied pursuant to the REMS program. In this regard, while the first set of verification qualifications may be limited to those that can be checked based upon the data associated with the prescription order itself, the second set of verification qualifications may include the evaluation of data from the prescription claim that was not provided with the original order, but that is the product of processing of the order and/or that has otherwise been added, such as by the service provider 12, the prescriber 72 or the pharmacy 74, following the initial submission of the order.

In an instance in which the apparatus 20, such the processing circuitry 22, determines that the second set of verification checks is not satisfied, such as in an instance in which one or more of the data elements extracted from the prescription claim differ from and do not satisfy the verification qualifications associated with the REMS program, such as defined by the information stored by the database 12*a*, the apparatus of an example embodiment includes means, such as the processing circuitry, the communication interface 26 or the like, for notifying the pharmacy 74 of the verification failure. See block 110 of FIG. 5B. In this regard, the notification may identify the particular verification qualification(s) that were not satisfied and/or may identify the data element(s) extracted from the prescription claim that failed to satisfy the verification qualifications. See blocks 174 and 176 of FIG. 7B. In some example embodiments, the notification may also provide information regarding how the particular verification qualification(s) can be satisfied, such that the pharmacy is better informed in relation to modifying the prescription claim to subsequently satisfy the verification qualifications of the REMS program. The pharmacy then has the option to modify the prescription claim, such as by modifying one or more data elements of the claim, in order to satisfy the verification qualifications associated with the REMS program and to then resubmit the claim for further evaluation. See block 178 of FIG. 7B. Alternatively, the pharmacy may choose to no longer pursue the prescription claim, such as by not providing the medication that is the subject of the prescription order, by not seeking at least partial payment by the PBM/Payer 76 or by providing the medication outside of the REMS program as a result of the failure to satisfy the verification qualifications associated with the REMS program under which the prescription order and claim were previously submitted.

In an instance in which the second set of verification checks is satisfied, however, the apparatus 20 includes means, such as the processing circuitry 22, the communication interface 26 or the like, for causing the claim to be submitted via an adjudication network for adjudication, such as by the PBM/payer 76. See block 112 of FIG. 5B, operation 6 of FIG. 6 and block 180 of FIG. 7B. As shown in blocks 182 and 184 of FIG. 7B, the PBM/payer adjudicates the prescription claim to determine the amount, if any, to be paid by the payer or other third party and then returns a response to the prescription claim. Following the adjudication, the apparatus includes means, such as the processing circuitry, the communication interface or the like, for receiving the response, such as from the PBM/payer as shown with operation 7 of FIG. 6, and for determining whether the response approves of the prescription claim. See block 114 and 116 of FIG. 5B and block 186 of FIG. 7B. In this regard, the response may indicate that the prescription claim has been approved, such as in an instance in which the PBM/payer indicates that the medication that is the subject of the prescription order with which the prescription claim is associated will be paid, either entirely or at least partially, by a third-party payor. Alternatively, the response may indicate that the claim has been disapproved, such as in an instance in which the medication that is the subject of the prescription order with which the prescription claim is associated will not be paid by a third-party payor.

In an instance in which the response indicates that the prescription claim has not been approved for payment, the apparatus 20 of an example embodiment includes means, such as the processing circuitry 22, the communication interface 26 or the like, for notifying the pharmacy 74 of the adjudication failure. See block 118 of FIG. 5B and block 188 of FIG. 7B. In this regard, the notification may identify the reason(s) as why the prescription claim was not approved, if the response from the PBM/payer 76 provides the reason(s). The pharmacy then has the option to modify the prescription claim, such as by modifying one or more data elements of the claim, in order to address the reason(s) for the prior disapproval of the claim and to then resubmit the claim for further evaluation. See block 178 of FIG. 7B. Alternatively, the pharmacy may choose to no longer pursue the prescription claim, such as by not providing the medication that is the subject of the prescription order or by not seeking at least partial payment by the PBM/payer.

However, in an instance in which the response indicates that the prescription claim has been approved, the apparatus 20 includes means, such as the processing circuitry 22 or the like, for generating a second indication of the satisfaction of the second set of verification checks, such as an authorization ID. The apparatus of this example embodiment includes means, such as the processing circuitry or the like, for associating the second indication with the response. See block 120 of FIG. 5B and block 190 of FIG. 7B. The second indication may be associated with the response in various manners. In one embodiment, however, the apparatus, such as the processing circuitry, is configured to modify the response so as to include the authorization ID, thereby serving to indicate that the second set of verification checks has been satisfied. In this regard, the response may include a data field that was not previously utilized, but that may now be populated with the second indication, such as the authorization ID that is generated by the service provider 12. In addition, the apparatus, such as the processing circuitry, the memory 24 or the like, of an example embodiment is configured to store the second indication, such as the authorization ID, such as in the database 12a, in association with the prescription claim and/or the prescription order. See block 124 of FIG. 5A. The second indication, such as the authorization ID, may be stored for various purposes including tracking of the prescription status as described below.

The apparatus 20 of this example embodiment also includes means, such as the processing circuitry 22, the communications interface 26 or the like, for causing the response including the associated second indication, such as the authorization ID, to be provided to the pharmacy 74. See block 122 of FIG. 5B, operation 8 of FIG. 6 and block 192 of FIG. 7B. The pharmacy receives the response, including the second indication, e.g., the authorization ID, as shown in block 194 of FIG. 7B and may then fulfill the prescription order from the prescriber 72, such as by providing the medication that was the subject of the prescription order to the patient pursuant to the REMS program.

In accordance with an example embodiment described above in which the pharmacy 74 that receives the prescription order looks to a different party, such as the PBM/payer 76 or other third party, for at least a portion of the payment for the medication that is the subject of the order, the apparatus 20 includes means, such as the processing circuitry 22 or the like, for monitoring the adjudication network established by or with the PBM/payer in order to monitor the status of the order, after the response including the second indication has been provided to the pharmacy. See block 126 of FIG. 5B and block 196 of FIG. 7B. In this regard, after receipt of the prescription order, the medication that is the subject of the order may not be provided by the pharmacy to the patient for some time, if at all, such as in an instance in which the patient fails to pick up the medication from the pharmacy.

By monitoring the adjudication network, the apparatus 20, such as the processing circuitry 22, is configured to identify an instance in which the status of the prescription order changes from a final claim status that was established upon the pharmacy 74 being provided with the response and the second indication, such as the authorization ID. In this regard, the apparatus, such as the processing circuitry or the like, is configured to identify the change in status of the prescription order, such as to a paid status, and to correlate the change in status to the provision of the medication that is the subject of the prescription order by the pharmacy to the patient. See block 198 of FIG. 5B. Thus, the apparatus of this example embodiment may include means, such as the processing circuitry, the communication interface 26 or the like, for providing a notification, such as a fill notice, to the prescriber 72 that submitted the prescription order in response to the order having a predetermined status, such as a paid status, that is indicative of the order having been provided to the patient. See block 128 of FIG. 5B and blocks 200 and 202 of FIG. 7B.

As a result of monitoring the adjudication network and providing a notification in an instance in which the order has a predetermined status, the prescriber 72 that submitted the prescription order is assured of receiving feedback in an instance in which the order is provided to the patient. In this regard, the apparatus 20, such as the processing circuitry 22, the communication interface 26 or the like, may be configured to monitor the adjudication network for a predefined period of time. Thus, the prescriber is assured of receiving a response regarding the status of the prescription order within the predefined period of time, such as an indication that the medication that is the subject of the order has been provided to the patient or that the medication that is the subject of the order has not been provided to the patient (in an instance in which the predefined period of time expires without a change in the order status). Consequently, the prescriber has less incentive to resubmit the order out of concern that the initial order was misdirected or otherwise not successfully received and processed and correspondingly reduces the burden upon the communication network and/or the computing devices of the various parties relative to instances in which the prescriber resubmits the order.

As noted above, FIGS. 3A, 3B, 5A, 5B, 7A and 7B are flowcharts illustrating the operations performed by a method, apparatus and computer program product, such as apparatus 20 of FIG. 2, in accordance with one embodiment of the present invention. It will be understood that each block of the flowcharts, and combinations of blocks in the flowcharts, may be implemented by various means, such as hardware, firmware, processor, circuitry and/or other device associated with execution of software including one or more computer program instructions. For example, one or more of the procedures described above may be embodied by computer program instructions. In this regard, the computer program instructions which embody the procedures described above may be stored by a memory 24 of a computing device employing an embodiment of the present invention and executed by a processing circuitry 22 of the apparatus. As will be appreciated, any such computer program instructions may be loaded onto a computer or other programmable apparatus (e.g., hardware) to produce a machine, such that the resulting computer or other programmable apparatus provides for implementation of the functions specified in the flowchart blocks. These computer program instructions may also be stored in a non-transitory computer-readable storage memory that may direct a computer or other programmable apparatus to function in a particular manner, such that the instructions stored in the computer-readable storage memory produce an article of manufacture, the execution of which implements the function specified in the flowchart blocks. The computer program instructions may also be loaded onto a computer or other programmable apparatus to cause a series of operations to be performed on the computer or other programmable apparatus to produce a computer-implemented process such that the instructions which execute on the computer or other programmable apparatus provide operations for implementing the functions specified in the flowchart blocks. As such, the operations of FIGS. 3A, 3B, 5A, 5B, 7A and 7B, when executed, convert a computer or processing circuitry into a particular machine configured to perform an example embodiment of the present invention. Accordingly, the operations of FIGS. 3A, 3B, 5A, 5B, 7A and 7B define an algorithm for configuring a computer or processing circuitry, e.g., processor, to perform an example embodiment. In some cases, a general purpose computer may be provided with an instance of the processor which performs the algorithm of FIGS. 3A, 3B, 5A, 5B, 7A and 7B to transform the general purpose computer into a particular machine configured to perform an example embodiment.

Accordingly, blocks of the flowcharts support combinations of means for performing the specified functions and combinations of operations for performing the specified functions. It will also be understood that one or more blocks of the flowcharts, and combinations of blocks in the flowcharts, can be implemented by special purpose hardware-based computer systems which perform the specified functions, or combinations of special purpose hardware and computer instructions. In some embodiments, certain ones of the operations above may be modified or further amplified and additional optional operations may be included. It should be appreciated that each of the modifications, optional additions or amplifications below may be included with the operations above either alone or in combination with any others among the features described herein.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A multi-stage verification method, the method comprising:
   extracting data from an order for a prescription submitted by a source computer associated with a prescriber, wherein the prescription is pursuant to a program having a plurality of verification qualifications;
   performing a first set of verification checks by at least comparing data extracted from the order to information stored in a database to determine if the order satisfies the first set of verification checks, wherein the information stored in the database identifies a plurality of required verification qualifications;
   in an instance in which the first set of verification checks is satisfied, modifying the order to include a first indication of satisfaction of the first set of verification checks;
   in an instance in which the first set of the verification checks is not satisfied, causing transmission of a notification message to the source computer, and halting further processing and preventing adjudication of the order until the order is modified and resubmitted by the source computer associated with the prescriber; and
   further in the instance in which the first set of verification checks is satisfied:
      extracting data from a claim for the prescription that is transmitted by a fulfillment computer associated with a pharmacy, wherein the claim is based upon the order, wherein the claim includes the first indication that the first set of verification checks was satisfied;
      performing a second set of verification checks based upon the data extracted from the claim and including at least some data not included in or associated with the order, wherein the second set of verification checks includes one or more verification checks that are different than the first set of verification checks, and the one or more verification checks of the second set of verification checks comprises one or more verification checks of action taken in response to the order; and
      in an instance in which the second set of verification checks is satisfied, submitting the claim via an adjudication network for adjudication.

2. The multi-stage verification method of claim 1, wherein the one or more verification checks of the second set of verification checks comprises one or more verification checks that are dependent upon a timing associated with the order.

3. The multi-stage verification method of claim 1, wherein the one or more verification checks of the second set of verification checks comprises a verification of validity of the first set of verification checks.

4. The multi-stage verification method of claim 1, wherein the one or more verification checks of the second set of verification checks include one or more verification checks that were also included in the first set of verification checks.

5. The multi-stage verification method of claim 1 further comprising:
   receiving an approval response following the adjudication; and
   associating a second indication of satisfaction of the second set of verification checks with the approval response.

6. The multi-stage verification method of claim 1, wherein the notification message transmitted to the source computer comprises an identification of one or more verification qualifications that were not satisfied or an identification of one or more data elements extracted from the order that failed to satisfy one or more verification qualifications.

7. The multi-stage verification method of claim 1, wherein the source computer that submits the order on which the first set of verification checks is performed, is associated with a prescriber and the fulfillment computer that transmits the claims on which the second set of verification checks is performed is associated with a pharmacy.

8. An apparatus configured to conduct a multi-stage verification, the apparatus comprising:
   a communication interface configured to receive an order for a prescription submitted by a source computer associated with a prescriber, wherein the prescription is, pursuant to a program having a plurality of verification qualifications; and
   processing circuitry configured to extract data from the order, to perform a first set of verification checks by at least comparing data extracted from the order to information stored in a database to determine if the order satisfies the first set of verification checks, wherein the information stored in the database identifies a plurality of required verification qualifications, in an instance in which the first set of verification checks is satisfied, to modify the order to include a first indication of satisfaction of the first set of verification checks, to extract data from a claim for the prescription that is transmitted by a fulfillment computer associated with a pharmacy, wherein the claim and that is based upon the order and that includes the first indication that the first set of verification checks was satisfied and to perform a second set of verification checks based upon the data extracted from the claim and including at least some data not included in or associated with the order, wherein the second set of verification checks includes one or more verification checks that are different than the first set of verification checks, and the one or more verification checks of the second set of verification checks comprises one or more verification checks of action taken in response to the order, and
   wherein the communication interface is further configured, in an instance in which the first set of the verification checks is not satisfied, to transmit a notification message to the source computer and halt further processing and preventing adjudication of the order until the order is modified and resubmitted by the source computer associated with the prescriber, and in an instance in which the second set of verification checks is satisfied, to submit the claim via an adjudication network for adjudication.

9. The apparatus of claim 8, wherein the one or more verification checks of the second set of verification checks that are different than the first set of verification checks comprises one or more verification checks of action taken in response to the order.

10. The apparatus of claim 8, wherein the one or more verification checks of the second set of verification checks comprises one or more verification checks that are dependent upon a timing associated with the order.

11. The apparatus of claim 8, wherein the one or more verification checks of the second set of verification checks comprises a verification of validity of the first set of verification checks.

12. The apparatus of claim 8, wherein the one or more verification checks of the second set of verification checks include one or more verification checks that were also included in the first set of verification checks.

13. The apparatus of claim 8 wherein the communication interface is further configured to receive an approval response following the adjudication, and wherein the processing circuitry is further configured to associate a second indication of satisfaction of the second set of verification checks with the approval response.

14. A computer program product configured to conduct a multi-stage verification, the computer program product comprising at least one non-transitory computer-readable storage medium having computer-executable program code instructions stored therein, the computer-executable program code instructions comprising program code instructions configured to:
   extract data from an order for a prescription submitted by a source computer associated with a prescriber, wherein the prescription is pursuant to a program having a plurality of verification qualifications;
   perform a first set of verification checks by at least comparing data extracted from the order to information stored in a database to determine if the order satisfies the first set of verification checks, wherein the information stored in the database identifies a plurality of required verification qualifications;
   in an instance in which the first set of verification checks is satisfied, modify the order to include a first indication of satisfaction of the first set of verification checks;
   in an instance in which the first set of the verification checks is not satisfied, transmit a notification message to the source computer and halt further processing and preventing adjudication of the order until the order is modified and resubmitted by the source computer associated with the prescriber;
   further in the instance in which the first set of verification checks is satisfied;
      extract data from a claim for the prescription that is transmitted by the fulfillment computer associated with a pharmacy, wherein the claim is based upon the order, wherein the claim includes the first indication that the first set of verification checks was satisfied;
      perform a second set of verification checks based upon the data extracted from the claim and including at least some data not included in or associated with the order, wherein the second set of verification checks includes one or more verification checks that are different than the first set of verification checks, and the one or more verification checks of the second set of verification checks comprises one or more verification checks of action taken in response to the order; and
      in an instance in which the second set of verification checks is satisfied, submit the claim via an adjudication network for adjudication.

15. The computer program product of claim 14 wherein the computer-executable program code instructions further comprise program code instructions configured to:
   receive an approval response following the adjudication; and
   associate a second indication of satisfaction of the second set of verification checks with the approval response.

* * * * *